United States Patent [19]

Holden

[11] 4,172,890

[45] Oct. 30, 1979

[54] 2,3,4,5-TETRAHYDRO-1H-3-BENZAZEPINE-7,8-DIONES

[75] Inventor: Kenneth G. Holden, Haddonfield, N.J.

[73] Assignee: SmithKline Corporation, Philadelphia, Pa.

[21] Appl. No.: 904,823

[22] Filed: May 11, 1978

Related U.S. Application Data

[62] Division of Ser. No. 783,574, Apr. 1, 1977, Pat. No. 4,108,989.

[51] Int. Cl.$^2$ .................... A61K 31/38; A61K 31/55; C07D 223/16
[52] U.S. Cl. ................................ 424/244; 260/330.3; 260/347.3; 260/347.8; 424/275
[58] Field of Search ............ 260/329 F, 346.22, 347.8, 260/347.3, 347.7; 424/244, 275

[56] References Cited

U.S. PATENT DOCUMENTS

| | | | |
|---|---|---|---|
| 3,609,138 | 9/1971 | DeStevens | 260/329 F |
| 3,686,167 | 8/1972 | Fujiimura et al. | 260/239 BB |

*Primary Examiner*—Donald G. Daus
*Assistant Examiner*—D. B. Springer
*Attorney, Agent, or Firm*—Joseph A. Marlino; Richard D. Foggio; William H. Edgerton

[57] ABSTRACT

Novel benzazepine derivatives having central and peripheral dopaminergic activity useful in treating Parkinson's and cardiovascular diseases. The compounds have additional use as intermediates for the synthesis of other benzazepines with similar useful properties. The 1-phenyl-2,3,4,5-tetrahydro-1H-3-benzazepine-7,8-dione derivatives are particularly useful.

9 Claims, No Drawings

2,3,4,5-TETRAHYDRO-1H-3-BENZAZEPINE-7,8-DIONES

This is a divisional of application Ser. No. 783,574, filed Apr. 1, 1977, now U.S. Pat. No. 4,108,989.

This invention relates to novel derivatives of 1-phenyl-2,3,4,5-tetrahydro-1H-3-benzazepines having valuable pharmacodynamic activity. More specifically, these compounds are stimulants of the central and peripheral dopamine receptors and are useful in the treatment of Parkinson's and cardiovascular diseases.

Further, the compounds have particular utility as intermediates for the synthesis of other benzazepines with similar useful properties. Advantageously the compounds of this invention can be employed in the preparation of lower alkylthio-7,8-dihydroxy-1-phenyl-2,3,4,5-tetrahydro-1H-3-benzazepines. For example, the 7,8-dione of Formula 1 is reacted with the desired mercaptan (RSH) in a suitable inert organic solvent such as an alcoholic solvent, methanol or ethanol to give a mixture of the 6- and 9-lower alkylthio containing isomers which can be easily separated into the 6 and 9 isomers by methods known to the art. If either the 6 or 9 position is occupied by a group the adding group will go to the unoccupied position.

The compounds of this invention can also serve as intermediates for the synthesis of 6-bromo or 6- and 9-chloro-7,8-dihydroxy-1-phenyl-2,3,4,5-tetrahydro-1H-3-benzazepines. The dione of Formula 1 is reacted with hydrogen bromide or hydrogen chloride by methods similar to the mercaptan addition in an inert organic solvent such as, for example, methylene chloride, to yield 6-bromo or a mixture of 6- and 9-chloro containing isomers. The mixture of isomers can be easily separated into the 6 or 9 isomer by methods known to the art.

The compounds of this invention are represented by the following general structural formula:

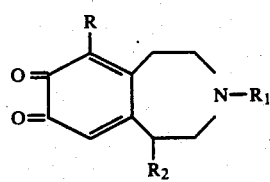

Formula 1 in which:
R is hydrogen or halo, especially chloro, fluoro or bromo;
$R_1$ is lower alkyl having from 1 to 5 carbon atoms, lower alkanoyl having from 1 to 5 carbon atoms such as formyl, acetyl or trifluoroacetyl, benzyl, phenethyl, carbobenzyloxy or hydroxyethyl; and
$R_2$ is thienyl, methylthienyl, furyl, phenyl or phenyl which is optionally substituted with a lower alkyl having from 1 to 5 carbon atoms preferably methyl, a halo such as fluoro, chloro, bromo or iodo, a lower alkoxy having from 1 to 4 carbon atoms preferably methoxy, hydroxy or methylthio.

Preferred compounds of this invention are represented by Formula 1 above when R is hydrogen, $R_1$ is hydrogen or methyl, and $R_2$ is phenyl or mono substituted phenyl. A particularly advantageous compound of Formula 1 is 1-phenyl-2,3,4,5-tetrahydro-1H-3-benzazepine-7,8-dione.

The pharmaceutically acceptable acid addition salts having the utility of the free bases of Formula 1, prepared by methods well known to the art, are formed with both inorganic or organic acids, for example: maleic, fumaric, benzoic, ascorbic, pamoic, succinic, bis-methylene-salicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. Similarly the quaternary salts include those prepared from organic halides such as methyl iodide, ethyl iodide, benzyl chloride and the like.

1-Phenyl-2,3,4,5-tetrahydro-1H-3-benzazepines have been described in U.S. Pat. No. 3,393,192; British Patent Specification No. 1,118,688; and Swiss Pat. No. 555,831, including general methods of preparation. However, these references disclose no 7,8-dione compounds falling within the scope of Formula 1 hereinabove. In addition there is no disclosure of the dopaminergic properties of such compounds and their utility in the biological or chemical methods of this invention. These references do disclose 7,8-dihydroxy substituted 1-phenyl-3-benzazepines and various intermediates therefor, some of which serve as starting materials for preparing the compounds of this invention.

It will be obvious to one skilled in the art that the compounds of Formula 1 may be present as diastereoisomers which may be resolved into d and l optical isomers. Resolution of the optical isomers may be conveniently accomplished by fractional crystallization of their salts with optically active acids from appropriate solvents. Unless otherwise specified herein or in the claims, it is intended to include all isomers, whether separated or mixtures thereof. Where isomers are separated, the desired pharmacological activity will usually predominate in one of the isomers.

The compounds of Formula 1 may be prepared by oxidation of a 7,8-dihydroxy substituted benzazepine of the formula:

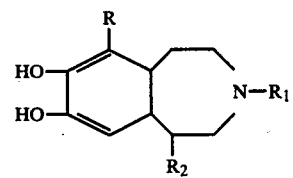

Formula II in which: R, $R_1$ and $R_2$ are described above.

The oxidation is preferably carried out with 2,3-dichloro-5,6-dicyano-1,4 benzoquinone in an inert organic solvent in which the reactants are soluble such as methanol ethanol usually in the cold at about 0-5° C. until the oxidation is complete. A number of other mild oxidizing agents known to convert catechols to o-quinones may be employed such as, for example, silver oxide, ceric ammonium nitrate, chloranil, silver carbonate, or succinidodimethyl-sulfonium cation.

The 7,8-dihydroxy substituted starting materials are either known to the art or are prepared by known methods such as the cyclization reactions described in U.S. Pat. Nos. 3,393,192 and 4,011,319.

The compounds of Formula 1 and their nontoxic pharmaceutically acceptable addition salts have a dopaminergic effect. They have a dual effect on dopamine receptors in the central nervous system notably the brain as well as on peripheral dopamine receptors such as those affecting the peripheral cardiovascular system.

The latter effect results in increased renal blood flow with a resulting hypotensive effect. It is often measured by administering the compound by infusion i.v. incrementally at five minute intervals to the anesthetized normotensive dog with measurement of various cardiovascular parameters. The effect on renal vasculator resistance can be calculated from any change in renal blood flow and arterial blood pressure. The effect is quantified as an $ED_{15}$ value which is the cumulative dose which produces a 15% decrease in renal vascular resistance $$(R = \frac{B.P. \text{ in mm/Hg.}}{B.F. \text{ ml/min.}}).$$

The compounds of Formula 1 have also been demonstrated as having antiParkinsonism activity due to central dopaminergic activity as demonstrated by employing a modified standard animal pharmacological test procedure reported by Ungerstedt et al., in *Brain Research* 24, 1970, 485–493. This procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling Parkinsonism, such as, for example, L-dopa and apomorphine, are also effective in this rat turning model. These compounds directly activate the dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$ value.

An advantageous compound of Formula 1, 1-phenyl-2,3,4,5-tetrahydro-1H-3-benzazepine-7,8-dione had an $ED_{15}$ of 280 mcg./kg. when tested for renal vasodilator activity and an $RD_{500}$ of 2.2 mg./kg. when tested in the above modified Ungerstedt test.

The compositions of this invention are prepared in conventional dosage unit forms by incorporating a compound of Formula 1 of a pharmaceutically acceptable salt thereof, in a nontoxic amount sufficient to stimulate central and peripheral dopamine receptors in an animal, with a nontoxic pharmaceutical carrier according to accepted procedures. Preferably the compositions 11 contain the active ingredient in an active but nontoxic amount selected from about 20 mg. to about 1000 mg. of active ingredient per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul or for i.v. infusion, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to the desired end product.

The method of producing dopaminergic activity in accordance with this invention comprises administering internally to an animal in need of such activity a compound of Formula 1 or a pharmaceutically acceptable salt thereof, usually combined with a pharmaceutical carrier, in a non-toxic amount sufficient to stimulate said peripheral dopamine receptors. The active ingredient will be administered preferably in a dosage unit, in an active, nontoxic quantity selected from about 20 mg. to about 1000 mg. of the parent chemical of Formula 1. The route of administration may be orally or parenterally, the oral route being preferred. Advantageously equal doses will be administered three times a day with the daily dosage regimen being selected from about 60 mg. to about 3000 mg. For administration by i.v. infusion, for example over a ten to thirty minute period, a total dose selected from about 0.5 mg. to about 50 mg. will be administered. When the method described above is carried out stimulation of peripheral dopamine receptors is produced with a minimum of side effects.

The following examples illustrate the preparation of specific compounds and pharmaceutical compositions having dopaminergic activity, specifically antiParkinsonism and cardiovascular activity. However, these examples should not be construed as a limitation of the invention since other variations will be obvious to those skilled in the art.

In the following examples the infrared absorption maxima for the carbonyl groups of the 7,8-diones were measured in nujol mulls and are reported in microns ($\mu$). The positions of the C-6 and C-9 protons in the nmr spectra of the 7,8-diones were measured at 60 $MH_2$ in $CDCl_3$-$DMSO,D_6$ (1:1) and are reported in delta units ($\delta$).

EXAMPLE 1

To a suspension of 34 g. (.101 mole) of 7,8-dihydroxy-1-phenyl-2,3,4,5-tetrahydro-1H-3-benzazepine hydrobromide in 275 ml. of methanol was added a solution of 2,3-dichloro-5,6-dicyano-1,4-benzoquinone (25.2 g. 0.111 mole) in 125 ml. of methanol. The addition was carried out rapidly with stirring at 0° under an argon atmosphere. After stirring at 0° for one hour, the reaction mixture was filtered and the precipitate washed with cold methanol (75 ml), ethyl acetate (100 ml) and then diethyl ether (100 ml). After drying at room temperature under vacuum 1-phenyl-2,3,4,5-tetrahydro- 1H-3-benzazepine-7,8-dione hydrobromide was obtained, m.p. 164°–165° (dec); ir:6.00, 6.08; nmr:6.38 (6H), 5.42 (9H).

EXAMPLE 2

Sodium hydride (57%, 4.84 g., 0.115 mole) previously washed with hexane is stirred with 70 ml. of dimethylsulfoxide at 65°–70° C. for two hours under dry argon. The mixture is diluted with 70 ml. of dry tetrahydrofuran, cooled to −5° C. and 23.5 g. (0.115 mole) of trimethylsulfonium iodide in 100 ml. of dry dimethyl sulfoxide is added over a period of several minutes. After stirring for one minute, 11.9 g. (0.0926 mole) of m-tolualdehyde is added at a moderate rate maintaining the temperature at 0° to −5° C. The mixture is stirred at 0° C. for five minutes and at room temperature for one hour, diluted with 500 ml. of ice-water and extracted with ether. The extract is washed with saturated sodium chloride solution, dried and evaporated to an oil, m-methylstyrene oxide.

A mixture of 14.5 g. (0.0797 mole) of 3,4-dimethoxyphenethylamine and 10.7 g. (0.0797 mole) of m-methylstyrene oxide is stirred at 100° C. under argon for 16 hours and then diluted with benzene. Cooling in ice precipitates N-[2-(3,4-dimethoxyphenyl)ethyl]-2-hydroxy-2-(3-methylphenyl)-ethylamine, m.p 95.5°–97° C.

The above prepared ethylamine (9.6 g., 0.0304 mole) is refluxed in 65 ml. of 48% hydrobromic acid for two hours under argon. Cooling yields the product 7,8-dihydroxy-1-(3-methylphenyl)-2,3,4,5-tetrahydro-1H-3-benzazepine hydrobromide, m.p. 108°–110° C.

The above compound is reacted with 2,3-dichloro-5,6-dicyano-1,4-benzoquinone in methanol as in Example 1 to give 1-(3-methylphenyl)-2,3,4,5-tetrahydro-1H-3-benzazepine-7,8-dione hydrobromide.

Following the above procedure and substituting o-tolualdehyde for m-tolualdehyde as a starting material yields 1-(2-methylphenyl)-2,3,4,5-tetrahydro-1H-3-benzazepine-7,8-dione; ir:6.05; nmr:6.39 (6H), 5.25 (9H).

EXAMPLE 3

A mixture of 42.0 g. of 57% sodium hydride dispersed in oil and 700 ml. of dimethyl sulfoxide is stirred at 70°–75° C. for one to one and one-half hours. The solution is diluted with 700 ml. of dry tetrahydrofuran and cooled to 0° C., under nitrogen. A 200 g. (1.0 mole) sample of trimethylsulfonium iodide is added in portions, maintaining the temperature between 0°–5° C. The mixture is stirred for 15 minutes and then a solution of 70.4 g. (0.50 mole) of m-chlorobenzaldehyde in 300 ml. of dry tetrahydrofuran is added dropwise. The resulting mixture is stirred at room temperature for four hours, poured into water and extracted with ether. The extract is washed with brine, dried and evaporated in vacuo to leave m-chlorostyrene oxide.

A solution of 27.1 g. (0.1 mole) of N-benzyl-3,4-dimethoxyphenylethylamine and 23.3 g. (0.15 mole) of m-chlorostyrene oxide in 500 ml. of methanol is stirred and refluxed overnight. The methanol is removed in vacuo and the residual N-benzyl-N-[2-(3,4-dimethoxyphenyl)ethyl]-2-hydroxy-2-(3-chlorophenyl)ethylamine is reduced without further purification. This sample (0.01 mole) is dissolved in ether, acidified with ethereal hydrogen chloride and hydrochloride precipitates. The latter is dissolved in 90 ml. of methanol, the solution is added to a mixture of 0.5 g. of palladium-on-carbon in 10 ml. of ethyl acetate and the mixture is hydrogenated at room temperature for 90 minutes at 60 psi. The reaction mixture is filtered and the filtrate evaporated in vacuo to yield N-[2-(3,4-dimethoxyphenyl]-2-hydroxy-2-(3-chlorophenyl)ethylamine hydrochloride, m.p. 155°–157.5° C.

A solution of 6.0 g. (0.0161 mole) of the above prepared amine in 250 ml. of 48% hydrobromic acid is stirred and refluxed for three hours. The reaction mixture is evaporated to give 1-(3-chlorophenyl)-7,8-dihydroxy-2,3,4,5-tetrahydro-1H-3-benzazepine hydrobromide.

This compound is oxidized using the benzoquinone as in Example 1 to yield 1-(3-chlorophenyl)-2,3,4,5-tetrahydro-1H-3-benzazepine-7,8-dione hydrobromide; ir:6.01; nmr:6.40 (6H); 5.47 (9H).

EXAMPLE 4

A mixture of 4.32 g. (0.0154 mole) of 7,8-dimethoxy-1-phenyl-2,3,4,5-tetrahydro-1H-3-benzazepine, 0.02 mole of n-butyl bromide and 0.02 mole of potassium hydroxide is dissolved in 120 ml. of dry methanol and refluxed for 48 hours. The reaction mixture is evaporated to dryness, taken up in ethyl acetate and filtered to remove inorganic salts. The filtrate is washed with water, dried and evaporated to give 3-n-butyl-7,8-dimethoxy-1-phenyl-2,3,4,5-tetrahydro-1H-3-benzazepine as an oil.

The 3-n-butyl benzazepine (0.0107 mole) is dissolved in 120 ml. of dry methylene chloride and 0.032 mole of boron tribromide is added dropwise at −10° C. The solution is warmed to room temperature and stirred for two hours. The excess boron tribromide is destroyed with methanol added dropwise with ice-cooling. The cold solution is refluxed on the steam bath to remove hydrogen bromide and then evaporated to yield 3-n-butyl-7,8-dihydroxy-1-phenyl-2,3,4,5-tetrahydro-1H-benzazepine hydrobromide, m.p. 231°–234° C.

The above compound is oxidized with the benzoquinone as in Example 1 to give 3-n-butyl-1-phenyl-2,3,4,5-tetrahydro-1H-benzazepine-7,8-dione hydrobromide.

EXAMPLE 5

A 3.3 g. (0.019 mole) quantity of 7,8-dihydroxy-1-phenyl-2,3,4,5-tetrahydro-1H-3-benzazepine (free base) was slurried in 40 ml. of dry acetone and 4.0 g. of anhydrous potassium carbonate was added. The mixture was stirred under nitrogen, a small amount of ascorbic acid was added as antioxidant and the mixture chilled to 0° and 1.57 g. (0.0129 mole) of allyl bromide was added. The mixture was stirred two to three hours in the cold and allowed to warm to ambient temperature and stirred an additional twelve hours. The mixture was then heated to reflux for thirty minutes and cooled, poured into water and extracted with three portions of ethyl acetate. Concentration of the combined extracts gave 2.7 g. of solid (71% crude yield). This was taken up in boiling ether and the solution allowed to stand for several hours. Filtration removed a small amount of precipitate and ethereal hydrogen chloride was then added to the filtrate to precipitate the hydrochloride salt which was isolated as an amorphous but non-hygroscopic solid, 2.0 g. on filtration and drying. Trituration of the solid with hot ethyl acetate followed by recrystallization from ethanol-ethyl acetate gave 0.85 g. of crystalline 3-allyl-7,8-dihydroxy-1-phenyl-2,3,4,5-tetrahydro-1H-3-benzazepine hydrochloride, m.p. 232°–234° (dec.).

This compound is reacted with quinone as in Example 1 to give 3-allyl-1-phenyl-2,3,4,5-tetrahydro-1H-3-benzazepine-7,8-dione hydrochloride.

Substituting phenethyl bromide in the above reaction gives the 3-phenethyl-1-phenyl-2,3,4,5-tetrahydro-1H-3-benzazepine-7.8-dione.

Further substituting the 3-methyl and 3-benzyl compounds and then oxidizing them with the benzoquinone of Example 1 gives 3-methyl-1-phenyl-2,3,4,5-tetrahydro-1H-3-benzazepine-7,8-dione hydrochloride; ir:601; nmr:6.41 (6H), 5.37 (9H); and 3-benzyl-1-phenyl-2,3,4,5-tetrahydro-1H-3-benzazepine-7,8-dione.

EXAMPLE 6

A solution of 7.10 g. (18.6 mole) of 7,8-dihydroxy-1-phenyl-2,3,4,5-tetrahydro-1H-3-benzazepine hydrobromide in 120 ml. of aqueous dimethyl-formamide at 0° under an argon atmosphere is basified to pH 10.0 with 10% sodium hydroxide solution. To this cold mixture is added 13.0 g. (76 mole) of carbobenzyloxy chloride in small portions over 15 minutes with concomitant addition of 10% alkali so as to maintain a pH of 10 to 10.5. The reaction is allowed to warm to room temperature after stirring at 0° for one and one-half hours. The mixture is diluted with saturated salt and extracted with three portions of ethyl acetate. The combined organic extract is backwashed twice with saturated salt. The dried extract is concentrated in vacuo and heated at 75°/0.1 mm Hg to remove any benzyl alcohol to yield 7,8-dihydroxy-N-carbobenzyloxy-1-phenyl-2,3,4,5-tetrahydro-1-H-3-benzazepine.

A solution of the above benzazepine (16.7 g.) in 150 ml. of ethyl acetate is stirred with silver oxide (36.6 g.) and anhydrous sodium sulfate (11.4 g.) under an argon atmosphere. The mixture is filtered and evaporated to give N-carbobenzyloxy-1-phenyl-2,3,4,5-tetrahydro-1-H-3-benzazepine-7,8-dione.

EXAMPLE 7

7,8-Dihydroxy-1-phenyl-2,3,4,5-tetrahydro-1H-3-benzazepine (5.0 g.) is suspended in 50 ml. of benzene. Trifluoroacetic anhydride (15 g.) is added dropwise rapidly. The solution is stirred an additional hour and then the volatiles are stripped off, leaving the N,O,O-tris-trifluoroacetyl derivatives. This is added directly to 50 ml. of methanol and hydrogen chloride gas is bubbled in for a few minutes. The reaction is stirred for 2 hours and the solvent stripped off, leaving a residue of 7,8-dihydroxy-1-phenyl-3-trifluoroacetyl-2,3,4,5-tetrahydro-1H-3-benzazepine.

The above compound is oxidized with silver oxide following the procedure of Example 6 to yield the 7,8-dione derivative.

EXAMPLE 8

A 3.7 g. (0.0145 mole) sample of 7,8-dihydroxy-1-phenyl-2,3,4,5-tetrahydro-1H-3-benzazepine free base was slurried in 25 ml. of acetone and 0.07 g. (0.016 mole, 10% excess) of ethylene oxide was added and the mixture placed in a pressure bottle and stirred at ambient temperature for 40 hours. The reaction mixture was heated to 60°-80° for thirty minutes, cooled and filtered. Concentration of the filtrate gave 4.5 g. of crystalline solid. This was taken up in ethyl acetate, reprecipitated by the addition of ether and converted to its hydrochloride salt by solution in ethanol, addition of ethereal hydrogen chloride and precipitation of the salt by additional ether to give 3.0 g. (yield 60%) on drying. Recrystallization from ethanol-ether gave 1.9 g. (yield 38%), m.p. 136°–137° of 7,8-dihydroxy-3-(2-hydroxyethyl)-1-phenyl-2,3,4,5-tetrahydro-1H-3-benzazepine hydrochloride.

The 2-hydroxyethyl compound (1.5 g.) is reacted with 2,3-dichloro-5,6-dicyano-1,4-benzoquinone in methanol as in Example 1 to give 3-(2-hydroxyethyl)-1-phenyl-2,3,4,5-tetrahydro-1H-3-benzazepine-7,8-dione hydrochloride.

EXAMPLE 9

A suspension of 4.84 g. of sodium hydride (57% mineral oil dispersion) in 70 ml. of dry dimethyl sulfoxide is heated at about 65° C. under argon with stirring for one hour. Dry tetrahydrofuran (75 ml.) is added and the resulting solution is cooled to −5° C. Trimethylsulfonium iodide (19 g., 92.8 mmole) is added very slowly and stirring is continued for about five minutes. A solution of 12.6 g. (92.8 mmole) of p-methoxybenzaldehyde in 120 ml. of tetrahydrofuran is added and the temperature is maintained at −5° C. After addition is completed the mixture is allowed to warm to room temperature, poured into water and extracted with ether. The extract is washed with saturated sodium chloride solution, dried and evaporated to give p-methoxystyrene oxide.

A mixture of 16 g. (88 mmole) of 3,4-dimethyloxyphenylethylamine and 13.5 g. (88 mmole) of p-methoxystyrene oxide is heated with stirring under argon on a steam bath overnight. A sample is withdrawn from the reaction mixture and chromatographed on a silica column, eluting with benzene ethyl acetate to isolate the pure product in crystalline form. To the remainder of the reaction mixture is added 100 ml. of ethyl acetate-hexane (1:1) and seeded with the crystalline product, with stirring and chilling. Filtration furnishes the product N-[2-(3,4-dimethoxyphenyl)-ethyl]-2-hydroxy-2-(4-methoxyphenyl)ethylamine, m.p. 92° C.

A solution of 4.4 g. (13.3 mmole) of the above prepared ethylamine in 20 ml. of 48% hydrobromic acid is heated at reflux under argon for two hours. Cooling precipitates 7,8-dihydroxy-1-(4-hydroxypheyl)-2,3,4,5-tetrahydro-1H-3-benzazepine hydrobromide, m.p. 287°–289° C.

The compound is oxidized using the 1,4-benzoquinone as in Example 1 to give 1-(4-hydroxyphenyl)-2,3,4,5-tetrahydro-1H-3-benzazepine-7,8-dione hydrobromide.

Following the above procedure and substituting m-methoxybenzaldenyde for p-methoxybenzaldehyde as a starting material yielded 1-(3-hydroxyphenyl)-2,3,4,5-tetrahydro-1H-3-benzazepine-7,8-dione hydrobromide; ir:6.03; nmr:6.38 (6H), 5.60 (9H).

EXAMPLE 10

A mixture of 8.9 g. (40 mmoles) of 1-hydroxy-7,8-dimethoxy-2,3,4,5-tetrahydro-1H-3-benzazepine and 5 ml. of thiophene in 45 ml. of trifluoroacetic is treated under argon at room temperature overnight. The volatiles are stripped off and the residue dissolved in 250 ml. of 3N hydrochloric acid. This acidic solution is washed with ether, basified with concentrated ammonium and extracted three times with ethyl acetate. The extracts are combined, washed with saturated brine and dried anhydrous potassium carbonate. The drying agent and solvent are removed to give 1-(2'-thienyl)-7,8-dimethoxy-2,3,4,5-tetrahydro-1H-3-benzazepine.

3.5 grams (12 mmoles) of 1-(2'-thienyl)-7,8-dimethoxy-2,3,4,5-tetrahydro-1H-3-benzazepine is dissolved in 60 ml. of methylene chloride and cooled to −12° by means of a methanol-ice bath, and 6 ml. (62 mmoles) boron tribromide is added dropwise. The resulting solution is stirred at room temperature for 1.5 hours and then evaporated at a brown residue under reduced pressure. The residue is cooled in ice and treated slowly with methanol. The methanol is evaporated at room temperature under reduced pressure. The residue is treated with methanol again and stripped under reduced pressure in a 50° hot-water bath. This treatment is repeated 3 times. The final residue is either chromatographed on a silica column eluted with 9:1 chloroform/methanol or dissolved in water. Any undissolved material is filtered off and the aqueous filtrate lyophilized to give pure 1-(2'-thienyl)-7,8-dihydroxy-2,3,4,5-tetrahydro-3-1H-benzazepine hydrobromide salt, m.p. 239°-240° (dec.).

The above compound is oxidized with the benzoquinone of Example 1 to give 1-(2'-thienyl)-2,3,4,5-tetrahydro-3-1H-benzazepine-7,8-dione.

EXAMPLE 11

Substituting 2-methyl-thiophene for thiophene as a starting material in and following the procedure of Example 10 yields 1-(5'-methyl-2'-thienyl)-2,3,4,5-tetrahydro-1H-3-benzazepine-7,8-dione; ir:6.00; nmr:6.35 (6H); 5.70 (9H).

In the same way using furan as a starting material in Example 10 yields 1-(2'-furyl)-2,3,4,5-tetrahydro-1H-3-benzazepine-7,8-dione.

EXAMPLE 12

A mixture of 11 g. (0.26 mole) of 57% sodium hydride and 183 ml. of dry dimethylsulfoxide was heated at 61°-66° for two hours. The mixture was cooled to room temperature and diluted with 183 ml. of dry tetrahydrofuran. The mixture was again cooled to −3° C. and a solution of 53.45 g. (0.26 mole) of trimethyl sulfonium iodide in 183 ml. of dry dimethylsulfoxide was added dropwise. Stirring was continued for five minutes and 19.2 g. (0.126 mole) of O-(methylthio)benzaldehyde in 20 ml. of dimethylsulfoxide was added with stirring overnight. The reaction was quenched on ice water and extracted with three 300 ml. portions of 1:1 benzene-ether. The combined extract was dried over magnesium sulfate and concentrated in vacuo to give O-(methylthio)phenylethylene epoxide.

The above epoxide (0.126 mole) was heated with 22.84 g. (0.126 mole) of homoveratrylamine at 110° for two hours under nitrogen at which time the reaction set solid. Thin layer chromatogram showed complete conversion and the product was crystallized from hot methanol and set overnight in a freezer. The mixture was filtered, washed with ether and air dried to give 20.0 g. of N-[β-hydroxy-O-(methylthio)-phenethyl]homoveratrylamine as white needles, m.p. 140°-142° C.

A solution of 5.0 g. (0.014 mole) of the amine in 50 ml. of 48% hydrogen bromide was heated at 80°-100° under nitrogen for one hour. The mixture was diluted with 100 ml. of water and concentrated in vacuo to yield a brown syrup. The syrup was diluted with 200 ml. of 50% isopropanol, treated with Darco and concentrated once again. The residual syrup was stripped several times from absolute ethanol and then triturated under 200 ml. of isopropanol, stirred in the cold and then refrigerated overnight. The solvent was decanted and slurried in ether. This was repeated and the solvent was pumped off at 1 min. Hg. The resulting powder became gummy. The material was peracetylated in pyridine, chromatographed on silica to yield 1-(2-methylthiophenyl)-7,8-dihydroxy-2,3,4,5-tetrahydro-1H-3-benzazepine hydrobromide.

The above benzazepine compound is reacted with 2,3-dichloro-5,6-dicyano-1,4 benzoquinone in methanol as in Example 1 to give 1-(2-methylthiophenyl)-2,3,4,5-tetrahydro-1H-3-benzazepine-7,8-dione hydrobromide; ir:5.93, 6.01; nmr:6.39 (6H), 5.25 (9H).

Following the above procedure and substituting p-(methylthio)benzaldehyde as a starting material for o-(methylthio)benzaldehyde yielded 1-(4-methylthiophenyl)-2,3,4,5-tetrahydro-1H-3-benzazepine-7,8-dione hydrobromide; ir:6.00; nmr:6.37 (6H), 5.46 (9H).

EXAMPLE 13

Isovanillin (200 g. 1.32 mole) was suspended in 1200 cc chloroform. Chlorine (103 g., 1.45 mole) was added by means of three 500 cc portions of carbon tetrachloride, in which it was dissolved. The suspension was stirred vigorously during the addition and the reaction was kept around 25° by a water bath. The suspension was stirred for 22 minutes after the completion of the addition of chlorine. The precipitate was filtered and crystallized from methanol, then recrystallized from isopropanol/ethyl acetate. Yield 98.7 g. (40%, m.p. 204°-206°) on 2-chloro-3-hydroxy-4-methoxybenzaldehyde.

The aldehyde product (189.3 g., 1.02 mole) was suspended in 1 liter of dry dimethylformamide, 350 g. of potassium carbonate was added. 145 cc (124 g., 1.54 mole) of dimethyl sulfate was added dropwise over a 20 minute period. After the addition the reaction was heated on the steam bath for 5 minutes. 70 cc. of water were added and the reaction was again heated for 5 minutes on the steam bath. The reaction was then poured into ice water and the precipitate was collected. It was crystallized from acetic acid/water (800 cc.-50cc.). A second crop was obtained from the mother liquor. Yield 180 g. (90%) of 2-chloro-3,4-dimethoxybenzaldehyde after drying, m.p. 69°-70°.

The dimethoxybenzaldehyde (180 g., 0.9 mole) was dissolved in 500 cc. warm acetic acid. 61 g. (0.8 mole) of ammonium acetate was added, followed by 160 cc. of nitromethane. The reaction was heated vigorously on the steam bath for 3 hours. Water was then added to the cloud point, while still heating, and the solution was cooled and scratched. The β-nitrostyrene began to oil out and then crystallized. The solution was cooled. The yellow crystals were collected and dried in a vacuum oven. Yield 175 g. (80% m.p. 88°-91°) of 2-chloro-3,4-dimethoxy-β-nitrostyrene.

The nitrostyrene (80 g., 0.33 mole) was dissolved in 800 cc. of dry tetrahydrofuran. Lithium aluminum hydride, as a 3.7 M solution (260 cc., 0.36 mole), was put in a 5 liter 3 neck flask which had been dried and flushed with argon. It was diluted with 500 cc. of dry ether. The solution of the nitrostyrene was added in a thin stream. The flask was cooled in an ice bath so that the heat of reaction caused a gentle reflux of the ether. After addition, the reaction was refluxed one hour, then worked up by adding 36 cc. of water, 36 cc. of 10% sodium hydroxide and 108 cc. of water sequentially and carefully, while cooling the reaction in ice.

The precipitate was collected, washed well with ethyl ether and discarded. The ether-tetrahydrofuran mixture was evaporated.

The above reaction was repeated on 83 g. of nitrostyrene. The two crude products were combined and distilled at 0.5 mm to collect at 142°–155° the product containing fraction which was pure 2-(2-chloro-3,4-dimethoxyphenyl)ethylamine by t.l.c. (80 g.).

The phenethylamine (25.7 g., 0.12 mole) was heated to 115° in an oil bath. Styrene oxide (14.4 g., 0.12 mole) was added and the reaction was heated for 1 hour. After cooling to ~30°, 2:1 petroleum ether/acetone was added to dissolve the oil; N-[(2-hydroxy-2-phenylethyl)]-N-[2-(2'-chloro-3',4'-dimethoxyphenyl)ethyl]amine, crystallized out in 37% yield (15 g.) m.p. 100°–101°.

The hydroxyphenethylamine (15 g. (0.0445 mole) was dissolved in 60 cc. of trifluoroacetic acid and 4.05 cc. of concentrated sulfuric acid was added. The reaction was refluxed 2 hours. After cooling most of the trifluoroacetic acid was stripped off and the residue was poured into water. It was made basic with 10% sodium hydroxide and was extracted with ether twice. The ether was dried, and as it was evaporated, a solid separated which was collected; m.p. 115°–121°, 6.0 g. of 6-chloro-7,8-dimethoxy-1-phenyl-2,3,4,5-tetrahydro-1H-3-benzazepine. The remaining ether was treated with ethereal hydrogen chloride and the hydrochloride salt precipitated; yield 3.2 g., total 62% m.p. 234°–236°. The dimethoxy derivative was converted to 6-chloro-7,8-dihydroxy-1-phenyl-2,3,4,5-tetrahydro-1H-3-benzazepine hydrobromide using boron tribromide in a 77% yield, m.p. 259°–260°.

The above compound is reacted with the benzoquinone as in Example 1 to yield 6-chloro-1-phenyl-2,3,4,5-tetrahydro-1-H-3-benzazepine-7,8-dione hydrobromide.

EXAMPLE 14

7,8-Dimethoxy-1-phenyl-2,3,4,5-tetrahydro-1H-3-benzazepine (280 g., 0.75 mole) was dissolved in 1700 cc. of acetic acid. Bromine (280 g., 1.75 mole) was added in a thin stream. The reaction was stirred for two hours. The precipitate, which formed after 1 hour, was collected and washed with ether. It was dissolved in boiling methanol and acetone was added to destroy the bromine excess. 6-Bromo-7,8-dimethoxy-1-phenyl-2,3,4,5-tetrahydro-1H-3-benzazepine hydrobromide was allowed to crystallize from the methanol and a second crop was obtained by adding ether to the mother liquor. Yield 298 g., 77% m.p. 236°–238°. This bromination may be applied to any 7,8-dialkoxy or alkanoyloxybenzazepine having a free 6-position.

The hydrobromide was shaken in a mixture of excess 10% sodium hydroxide and methylene chloride. The organic layer was separated, dried and evaporated to give a solid base which was crystallized from toluene-hexane; m.p. 125°–128°, yield 238 g. (97%).

The base (12 g., 0.033 mole) was dissolved in 200 cc. of methylene chloride and was cooled to −15° C. Boron tribromide (15.4 cc., 16 mole) was added cautiously. The reaction was allowed to run at room temperature for two hours. The solvent was stripped off and the flask was cooled to −15°. Dry methanol was added to destroy the boron tribromide complexes. It was then stripped off. The residue was crystallized from water, then boiled in acetonitrile to aid in the drying of the compound. Yield of 6-bromo-7,8-dihydroxy-1-phenyl-2,3,4,5-tetrahydro-1H-3-benzazepine hydrobromide; 10.26 g. (75%), m.p. 240°–242° after vacuum drying.

The 6-bromo compound is oxidized using the benzoquinone as in Example 1 to yield 6-bromo-1-phenyl-2,3,4,5-tetrahydro-1H-3-benzazepine-7,8-dione hydrobromide.

EXAMPLE 15

To a stirred suspension of 1-phenyl-2,3,4,5-tetrahydro-1H-3-benzazepine-7,8-dione (5 g., 0.015 mole) in 150 ml. of methanol was rapidly bubbled an excess of methyl mercaptan. The orange quinone quickly dissolved to give a pale yellow solution which was evaporated to a residue which was a mixture of 7,8-dihydroxy-6-methylthio and 9-methylthio-1-phenyl-2,3,4,5-tetrahydro-1H-3-benzazepine hydrobromide.

A mixture of the isomers (3.3 g.) was dissolved in 3.2 ml. of methanol and diluted to 80 ml. with chloroform. This solution was applied to a silica gel column (100 g., 4.5×15 cm) and eluted with a linear gradient composed of chloroform containing an increasing concentration of methanol (1000 ml., 5% to 20% methanol). The 6-isomer was eluted first followed by a mixture of 6-and 9-isomers and then the 9-isomer. Fractions containing the pure 6-isomer were combined and evaporated to a residue (1.4 g.) which was crystallized from ethanol-ethyl acetate to give 0.64 g. (0.0017 mole, 11%), m.p. 258° (dec.).

Anal. Calc'd for $C_{17}H_{19}NO_2S \cdot HBr$: C, 53.41; H, 5.27; N, 3.66; S, 8,39 Found: C, 53.41 H, 5.10; N, 3.55; S, 8.64.

Fractions containing the pure 9-isomer were evaporated to a residue and combined with the 2.2 g. obtained by direct crystallization. Recrystallization from methanol-ethyl acetate gave the pure 9-isomer (1.25 g., 0.0034 mole, 22%), m.p. 270° (dec.).

Anal. Calc'd for $C_{17}H_{19}NO_2S \cdot HBr$: C, 53.41;. H, 5.27; N, 3.66; S, 8.39. Found: C, 53.15; H, 5.33; N, 3.58; S, 8.24.

EXAMPLE 16

Under an argon atmosphere dry hydrogen chloride was bubbled into a stirred suspension of 1-phenyl-2,3,4,5-tetrahydro-1H-3-benzazepine-7,8-dione hydrochloride (1 g.) in 50 ml. of methylene chloride. After the initial color of the precipitate changed to an off-white color, the suspension was chilled and filtered to give a mixture of 6-chloro and 9-chloro isomers. These isomers were separated by chromatography on silica gel as described in Example 15. The separated isomers were recrystallized from methanol-ethyl acetate to yield respectively 6chloro-1-phenyl-7,8-dihydroxy-2,3,4,5-tetrahydro-1H-3-benzazepine hydrobromide and 9-chloro-1-phenyl-7,8-dihydroxy-2,3,4,5-tetrahydro-1H-3-benzazepine hydrobromide.

EXAMPLE 17

Under an argon atmosphere dry hydrogen bromide was bubbled into a stirred solution of 1-phenyl--2,3,4,5-tetrahydro-1H-3-benzazepine-7,8-dione hydrobromide (1.2 g.) in 60 ml. of methylene chloride. After the original orange color of the dione disappeared the product was filtered and recrystallized from methanol-ethyl acetate to yield the desired 6-bromo-phenyl-7,8-dihydroxy-2,3,4,5-tetrahydro-1H-3-benzazepine hydrobromide.

EXAMPLE 18

| Ingredients | Mg. per Capsule |
| --- | --- |
| 1-phenyl-2,3,4,5-tetrahydro-1H-3-benzazepine-7,8-dione | 125 (free base) |
| Magnesium Stearate | 2 |
| Lactose | 200 |

The above ingredients are thoroughly mixed and placed into hard gelatin capsules.

EXAMPLE 19

| Ingredients | Mg. per Tablet |
| --- | --- |
| 1-(3-methylphenyl)-2,3,4,5-tetrahydro-1H-3-benzazepine-7,8-dione hydrobromide | 200 (free base) |
| Corn Starch | 50 |
| Polyvinyl pyrrolidone | 12 |
| Magnesium Stearate | 3 |

A portion (30 mg.) of the corn starch and benzazepine are mixed and granulated with the polyvinyl pyrrolidone. The granules are dried, mixed with the remaining starch and magnesium stearate and compressed into tablets.

The capsules and tablets as prepared in Examples 18 and 19 are administered orally to an animal including a human requiring stimulation of dopamine receptors within the dose ranges set forth hereinabove. Similarly other compounds of Formula 1 or the other examples can be formulated in the same manner to give pharmaceutical compositions useful in the methods of this invention.

What is claimed is:

1. A compound of the formula:

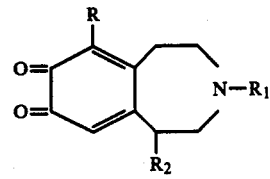

in which:
R is hydrogen or halo
$R_1$ is hydrogen, lower alkyl having from 1 to 5 carbon atoms, benzyl, phenethyl, or hydroxyethyl; and
$R_2$ is thienyl, methylthienyl or furyl, and the pharmaceutically acceptable nontoxic salts thereof.

2. The compound of claim 1 in which R is hydrogen and $R_1$ is hydrogen or methyl.
3. The compound of claim 2 in which $R_2$ is thienyl.
4. The compound of claim 2 in which $R_2$ is furyl.
5. A pharmaceutical composition in dosage unit form having dopaminergic activity comprising a pharmaceutical carrier and an effective therefor but nontoxic quantity of the compound of claim 1.
6. The method of producing dopaminergic activity in an animal in need of such activity which comprises administering internally a nontoxic sufficient amount of the compound of claim 1.
7. A chemical compound according to claim 2 in which R and $R_1$ are hydrogen and $R_2$ is thienyl
8. The compound of claim 7 in which the salt form is the hydrobromide.
9. A compound of the formula:

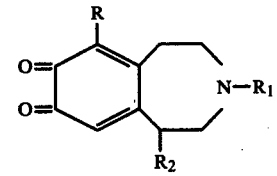

in which:
R is hydrogen or halo;
$R_1$ is lower alkanoyl having from 1 to 5 carbon atoms or carbobenzyloxy; and
$R_2$ is thienyl, methylthienyl or furyl; and the pharmaceutically acceptable nontoxic salts thereof.

* * * * *